United States Patent
Clough et al.

(10) Patent No.: US 7,350,918 B2
(45) Date of Patent: Apr. 1, 2008

(54) METHOD OF DESIGNING EQUAL CONIC INTRAOCULAR LENS

(75) Inventors: John Clough, St. Petersburg Beach, FL (US); Edwin J. Sarver, Carbondale, IL (US); Donald R. Sanders, Elmhurst, IL (US)

(73) Assignee: Lenstec Inc., St. Petersburg, FL (US)

( * ) Notice: Subject to any disclaimer, the term of this patent is extended or adjusted under 35 U.S.C. 154(b) by 0 days.

(21) Appl. No.: 11/452,134

(22) Filed: Jun. 13, 2006

(65) Prior Publication Data

US 2006/0279697 A1    Dec. 14, 2006

Related U.S. Application Data

(60) Provisional application No. 60/690,664, filed on Jun. 14, 2005.

(51) Int. Cl.
    *G02C 7/02* (2006.01)

(52) U.S. Cl. .................................................. 351/177
(58) Field of Classification Search ............ 351/160 R, 351/160 H, 177; 623/6.23
See application file for complete search history.

(56) References Cited

U.S. PATENT DOCUMENTS

| 5,815,239 A | * | 9/1998 | Chapman et al. | ............ 351/177 |
| 7,048,759 B2 | * | 5/2006 | Bogaert et al. | ............ 623/6.17 |

* cited by examiner

*Primary Examiner*—Scott J. Sugarman
(74) *Attorney, Agent, or Firm*—Claude E. Cooke, Jr.; Burleson Cooke L.L.P.

(57) ABSTRACT

An intraocular lens, with equal conic surfaces, is intended to replace the crystalline lens in the posterior chamber of a patient's eye, in particular after a cataract extraction. The lens provides optical power to focus objects onto a patient's retina. In addition the lens surfaces are shaped to reduce optical aberrations at the retina and are tolerant to lens tilt and decentration within the eye. The lens is designed to have zero longitudinal ray aberrations at a specific ray height.

3 Claims, 4 Drawing Sheets

MILLIMETERS

METHOD OF DESIGNING EQUAL CONIC INTRAOCULAR LENS

This application claims the benefit of U.S. Provisional Application No. 60/690,664 filed Jun. 14, 2005.

BACKGROUND OF THE INVENTION

1. Field of the Invention

The present invention pertains to intraocular lenses within the posterior chamber, and more particularly, to aspheric, conic, or prolate intraocular lenses within the posterior chamber.

2. Description of Related Art

It is often the case that an elderly patient will develop a condition called a cataract in the eye's crystalline lens. The cataract can develop to such a state that vision quality is significantly diminished to the point where surgical intervention is required to restore clear vision. In this surgical intervention, the crystalline lens containing the cataract is removed and an artificial lens is implanted. This artificial lens is called an intraocular lens (IOL). The IOL can be made of various materials, and its optical surfaces can be very simple such as planes, spheres, or torics, or the surfaces can be quite complex and even designed for a specific eye. The goal of the IOL design is, of course, to provide the patient with good vision quality. This means that the optical aberrations (deviation from a perfect focus) should be small. Over the last few decades the goal has been to provide the patient with a lens that significantly removes defocus and astigmatism. More recently, there has been an effort to remove other (higher-order) aberrations, such as spherical aberrations, through the IOL design.

The eye can be considered as an optical system with its specific set of ocular aberrations. Since the normal cornea adds positive spherical aberration, it is possible to design an IOL with negative spherical aberration to reduce the normal eye's total spherical aberrations. If the lens is placed in the correct position and orientation in a normal eye, the spherical aberrations will be reduced as desired. This is the ideal situation. However, it is often the case that a patient's eye will have a cornea that has had refractive surgery such as LASIK, PRK, or RK. In addition, the lens may be decentered or tilted within the eye. In these non-ideal situations, the patient's vision will no longer have the desired improvement over the traditional spherical lenses. If the situation is far enough from the ideal, the patient's vision would have been better with a traditional spherical IOL rather than the "improved" IOL designed for reduction of spherical aberration.

It is possible to consider a reasonable amount of IOL decentration and tilts during the design process and so develop an IOL that is more tolerant to these types of situations. Such considerations can lead to an IOL design where very little positive spherical aberrations are added to the positive spherical aberrations generated by the typical cornea. However, the IOL would not necessarily have the benefit of being an equal surface (both surfaces are the same) optic. Also, the amount of spherical aberration for the IOL should be the same for each lens power provided so that postoperative results are more predictable. This can be measured using the longitudinal ray aberrations for the IOL. It is the objective of the present invention to provide a foldable IOL design that retains the benefits of an aspheric IOL that reduces spherical aberrations and additionally, is an equal surface design and has the same longitudinal ray aberrations characteristic for each IOL power.

SUMMARY OF INVENTION

In this section we describe how a foldable IOL can be designed with powers from −10 to +35 D (or larger range) with the characteristics that (1) the surfaces are equal, (2) provide the same longitudinal ray aberration characteristic for each lens power, and (3) add essentially zero spherical aberrations to the eye's ocular aberrations. In the preferred embodiment, parameters common to all powers of IOLs are: optical lens diameter of 5.75 mm, lens edge thickness of 0.35 mm, and material index of refraction of 1.4585 (polyhema). We refer to our lens design as the balanced aspheric IOL (B-IOL).

DETAILED DESCRIPTION

Figure 1A:
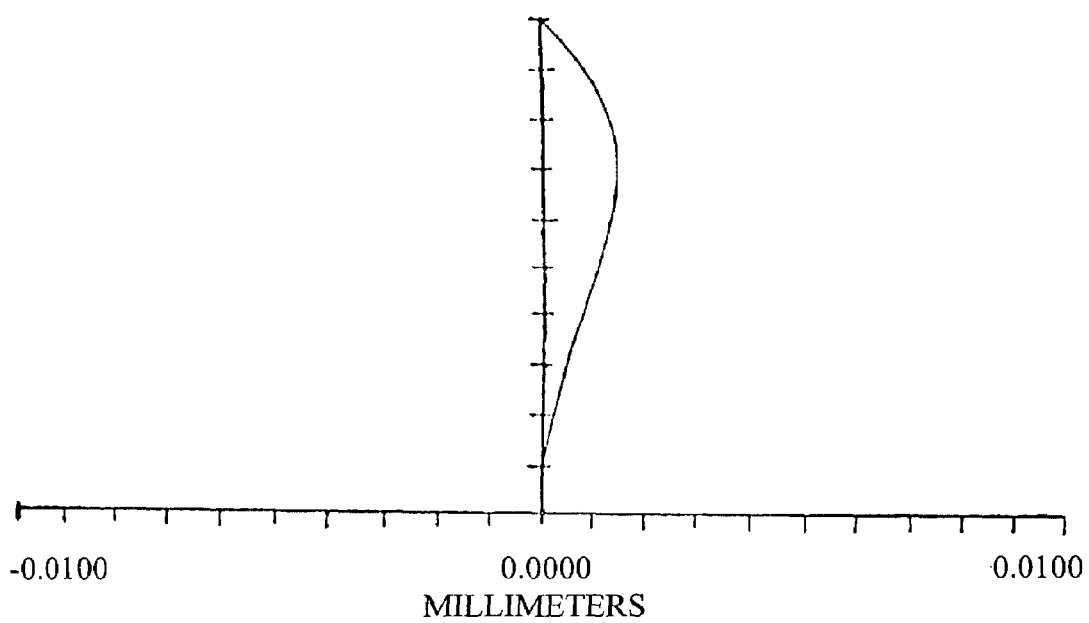
FIG. 1A illustrates longitudinal aberrations for a marginal ray that intersects paraxial focus.
Figure 1B:
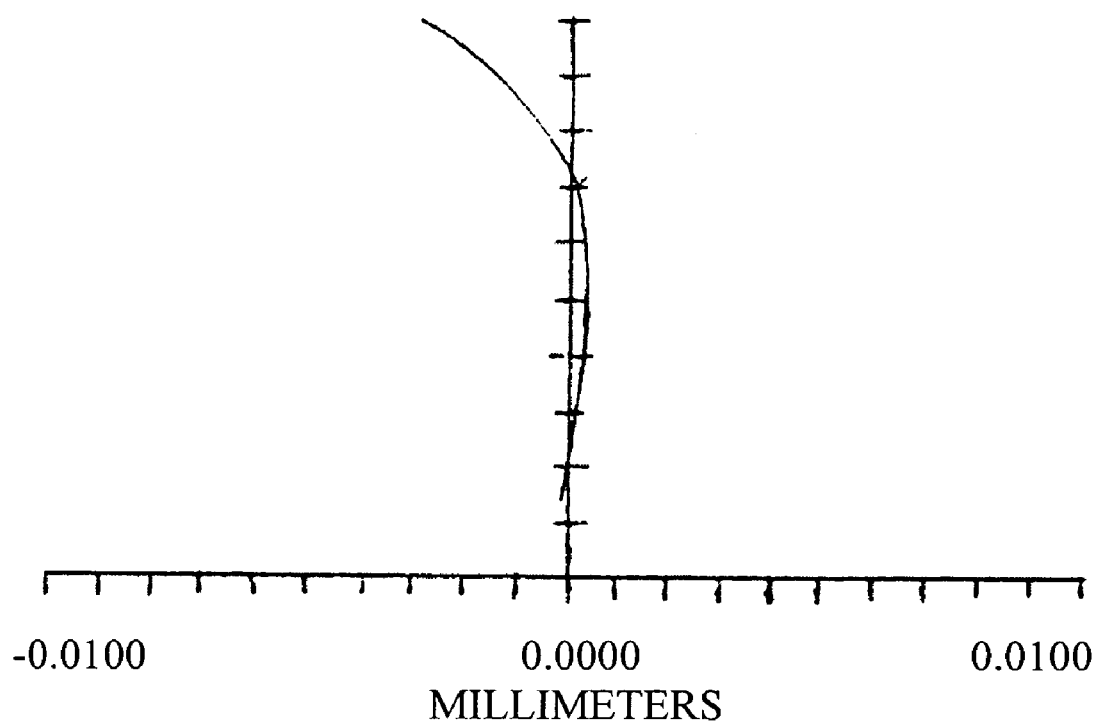
FIG. 1B illustrates longitudinal aberrations for a marginal ray height of 0.7071 times clear aperture radius.
Figure 2:
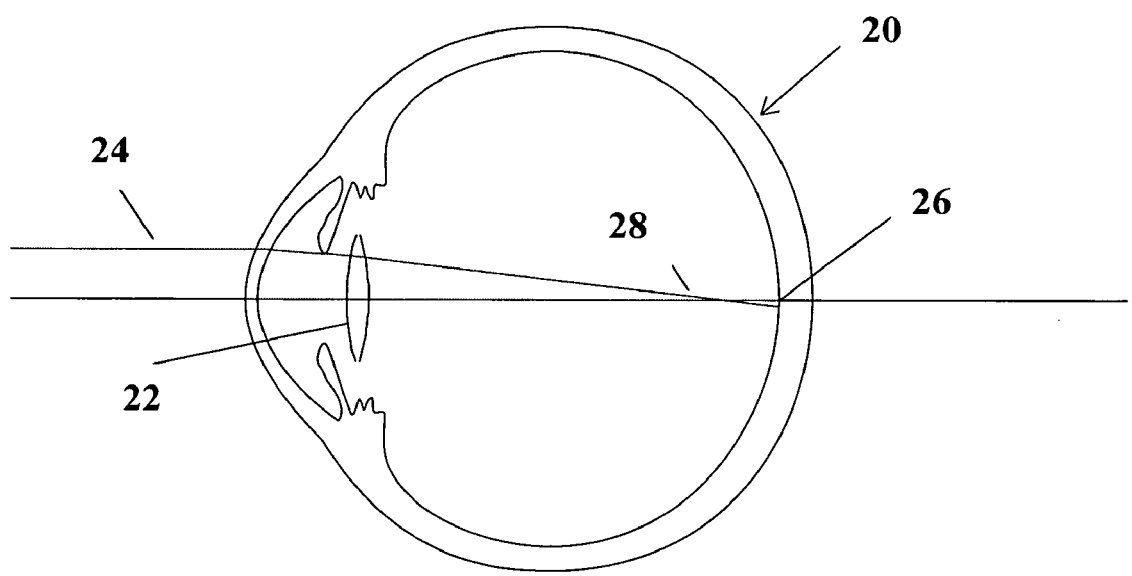
FIG. 2 illustrates the eye in cross section showing intersection of ray.

Given that the B-IOL must have symmetric surfaces (design requirement) and the paraxial power of the lens is the labeled power, the only true design parameter is the conic coefficient K. It is possible to set the conic constant so that the marginal ray (which just clears the edge of the clear aperture of the lens) for a distant object intersects the paraxial focus. The distance between the intersection of the off-axis ray with the optical axis and the paraxial focus is called the longitudinal aberration of the ray. For the case of zero longitudinal aberration at the marginal ray, the longitudinal aberration across the semi-diameter is graphed in FIG. 1.A. Note that in FIG. 1.A, the aberration at ray height of zero (the chief ray) is zero as is the ray at the edge of the lens. To reduce the overall sum of the longitudinal aberration, we can alternatively select the conic coefficient so that a ray at a height equal to 0.7071 of the clear aperture radius intersects the paraxial focus. This is illustrated in FIG. 1.B. The Seidel spherical aberration corresponding to FIG. 1.B is about half that represented in FIG. 1.A. Thus, the longitudinal aberrations are approximately "balanced". Our strategy is: select the conic coefficient that causes the parallel incident ray at a height of 0.7071 of the clear aperture radius to intersect the paraxial focus. This strategy is illustrated in FIG. 2, which shows eye 20 having lens 22. Parallel incident ray 24 enters the eye 20 at a height of 0.7071 times the radius of lens 22. Ray 24 is shown to be not focused on paraxial focus 26, which then requires an adjustment to K to cause ray 24 to focus at 26 and satisfy the strategy.

The conic constant K is well known in the optics field and is given by the surface equation for a conic:

$$z = \frac{\frac{s^2}{R}}{1 + \sqrt{1 - (1+K)\frac{s^2}{R^2}}} \quad (1)$$

where R is the apical radius, K is the conic constant ($K=-e^2$), and $s^2 = x^2 + y^2$. We are now ready to describe the method in which the lens parameters: apical radius, conic constant, and center thickness are computed.

Determining conic constant K for a given IOL power: As noted above the preferred embodiment has lens parameters: optical lens diameter of 5.75 mm, lens edge thickness of 0.35 mm, and material index of refraction of 1.4585. A sphere has a conic constant K=0. In our calculation of K to control the longitudinal ray aberrations, we use a starting value of K=0 and iterate over K until we have a longitudinal ray aberration of zero for an incident ray height of 0.7071 times the lens optical zone radius. This incident ray is referred to as the marginal ray. This iterative optimization is performed using a well known algorithm called Newton-Raphson iteration. The method requires two starting values for the parameter being optimized. Here we use K=0 and K=0.1. The method also requires two "error values" corresponding to the K values. The error value is this signed distance of where the final ray from the marginal ray crosses the optical axis minus the paraxial focus for the desired IOL power.

Figure 3:
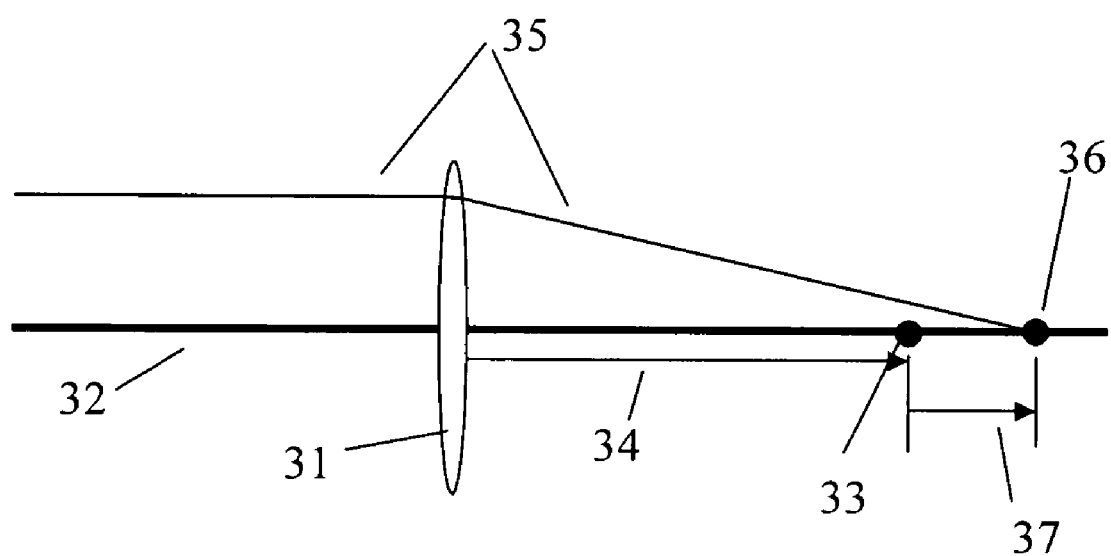
FIG. 3 illustrates geometry for ray tracing of marginal ray and calculation of longitudinal ray aberrations.

This is illustrated in FIG. 3 wherein the geometry for ray tracing of marginal ray and calculation of longitudinal ray aberrations is shown. The IOL 31 is centered on optical axis 32. The paraxial focus 33 is located a distance equal to the back focal length 34 from the back of the IOL 31. The marginal ray 35 intersects the optical axis at intersection point 36. The signed distance from the paraxial focus 33 to the marginal ray intersection point 36 is referred to as the longitudinal ray aberration 37.

In FIG. 3, the longitudinal ray aberration is denoted by item 37. To compute the location of the intersection point 36, we first need a complete description of the lens 31. Given the power Pe of the IOL and the current conic constant K, we need to compute the center thickness CT of the lens so that the edge thickness ET is the desired value (ET=0.35 for the preferred embodiment). Since the IOL has equal surfaces, the paraxial powers P of the anterior and posterior surfaces are equal. The apical radius R for the anterior surface is given by:

$$R = \frac{n1 - n0}{P} 1000 \qquad (2)$$

where n1 is the index of refraction of the IOL (1.4585), n0 is the index of refraction of the medium inside the eye (commonly taken as 1.336), P is the power of the anterior surface in diopters, and the apical radius R is given in mm. The sag Z for the anterior conic surface of the lens can be found using equation (1). Since we know the optical zone diameter OZ (OZ=5.75 mm in the preferred embodiment) and the edge thickness ET, we can compute the center thickness CT using (3).

$$CT = ET + 2 \times \frac{\frac{s^2}{R}}{1 + \sqrt{1 - (1+K)\frac{s^2}{R^2}}} \qquad (3)$$

$$s = \frac{OZ}{2}$$

The surface power (either surface since they are equal) can be computed from the desired IOL power Pe, the IOL index of refraction n1, and the center thickness CT using (4).

$$P = \frac{n - \sqrt{n(n - CT \times Pe)}}{CT} \qquad (4)$$

$$n = n1 \times 1000$$

It is evident that there is a dependence of the variables in equations (2), (3), and (4) on each other. Thus, we use an iteration loop over these equations until the apical radius R and the center thickness CT converge. We have empirically determined that a loop of 20 iterations is sufficient for all lens powers Pe in the range of −20 to 50 D. To start the iteration, we set P=Pe/2.

The back focal length bfl identified as item 34 in FIG. 3, can be computed from the paraxial relations given in equation (5).

$$Pv = P + \frac{1000 \times n1}{-CT + \frac{1000 \times n1}{P}} \qquad (5)$$

$$bfl = \frac{n0 \times 1000}{Pv}$$

Returning to the ray tracing illustrated in FIG. 3, for a given IOL power Pe and conic constant K, we can now describe how the longitudinal aberration is computed. An incident ray (left side of item 5 of FIG. 3) is parallel to the optical axis 32 at a height h=0.7071×OZ/2. We intersect the incident ray with the anterior surface of the IOL using a ray/conic intersection routine. Once the intersection is found, we compute the surface normal for the anterior surface and then refract the ray to determine its new direction. This refracted ray is then intersected and refracted with the posterior surface of the lens (separated by a distance CT from the anterior surface). The resulting refracted ray is then intersected with the optical axis to find the intersection point identified by item 36 in FIG. 3. These ray refraction and intersection calculations are well known to those familiar to the art. This intersection point 36 and the paraxial focus 33 found using equation (5) are subtracted to find the error used in the Newton-Raphson iteration described above. Thus, to find the error for a given conic constant K, we perform the following steps:

Error calculation:
1. Iterate over equations (2), (3), and (4) to find R and CT for a given Pe and K.
2. Find the paraxial focus point using equation (5)
3. Trace a marginal ray using the procedure described above and compute the ray intersection point item 36
4. Compute the error E=signed distance from point 36 to point 33.

In summary, to compute the apical radius R, conic constant K, and center thickness CT for an IOL of equivalent power Pe, we perform the following steps:

Lens parameters calculation:
1. Initialize
   a. Set K0=0 and K1=0.1
   b. Set E0 and E1=errors found using algorithm above
   c. NumIterations=0
   d. Set tol=1.0e-9
2. While NumIterations<10 and |E0−E1|>tol do the following steps
   a. NumIterations=NumIterations+1
   b. K=K0−E0×(K0−K1)/(E0−E1)

c. K0=K1
d. E0=E1
e. K1=K
f. E1=(error computed using algorithm for K1)
3. Compute R and CT by iteration over equations (2)-(4) using the final value of K Using this calculation approach we arrive at the example IOL design table shown below:

ASPHERIC IOL TABLE

Surrounding medium index = 1.3360
Material index = 1.4585
Edge thickness = 0.35
Lens diameter = 5.75
Lens_Power, R1 = −R2, K1 = K2, CT 4.00, 61.229627, −1.232115, 0.484977
4.50, 54.423361, −1.232072, 0.501852
5.00, 48.978206, −1.232028, 0.518728
5.50, 44.522950, −1.231983, 0.535604
6.00, 40.810119, −1.231937, 0.552480
6.50, 37.668382, −1.231889, 0.569357
7.00, 34.975364, −1.231841, 0.586235
7.50, 32.641319, −1.231791, 0.603112
8.00, 30.598941, −1.231740, 0.619990
8.50, 28.796759, −1.231688, 0.636868
9.00, 27.194740, −1.231634, 0.653746
9.50, 25.761280, −1.231580, 0.670624
10.00, 24.471094, −1.231524, 0.687502
10.50, 23.303715, −1.231467, 0.704379
11.00, 22.242397, −1.231409, 0.721257
11.50, 21.273304, −1.231350, 0.738135
12.00, 20.384910, −1.231290, 0.755012
12.50, 19.567531, −1.231228, 0.771890
13.00, 18.812971, −1.231165, 0.788766
13.50, 18.114252, −1.231101, 0.805643
14.00, 17.465390, −1.231036, 0.822519
14.50, 16.861227, −1.230970, 0.839395
15.00, 16.297295, −1.230902, 0.856270
15.50, 15.769698, −1.230834, 0.873145
16.00, 15.275032, −1.230764, 0.890019
16.50, 14.810302, −1.230693, 0.906892
17.00, 14.372866, −1.230621, 0.923765
17.50, 13.960386, −1.230547, 0.940637
18.00, 13.570781, −1.230473, 0.957508
18.50, 13.202197, −1.230397, 0.974379
19.00, 12.852974, −1.230320, 0.991248
19.50, 12.521623, −1.230242, 1.008117
20.00, 12.206803, −1.230163, 1.024985
20.50, 11.907305, −1.230082, 1.041852
21.00, 11.622035, −1.230001, 1.058718
21.50, 11.349999, −1.229918, 1.075583
22.00, 11.090296, −1.229834, 1.092447
22.50, 10.842102, −1.229749, 1.109309
23.00, 10.604668, −1.229662, 1.126171
23.50, 10.377307, −1.229574, 1.143031
24.00, 10.159389, −1.229486, 1.159891
24.50, 9.950336, −1.229396, 1.176749
25.00, 9.749615, −1.229304, 1.193605
25.50, 9.556738, −1.229212, 1.210461
26.00, 9.371251, −1.229119, 1.227315
26.50, 9.192735, −1.229024, 1.244168
27.00, 9.020805, −1.228928, 1.261019
27.50, 8.855099, −1.228831, 1.277869
28.00, 8.695286, −1.228732, 1.294718
28.50, 8.541054, −1.228633, 1.311565

ASPHERIC IOL TABLE-continued

Surrounding medium index = 1.3360
Material index = 1.4585
Edge thickness = 0.35
Lens diameter = 5.75
Lens_Power, R1 = −R2, K1 = K2, CT 29.00, 8.392116, −1.228532, 1.328410
29.50, 8.248201, −1.228430, 1.345254
30.00, 8.109059, −1.228327, 1.362097
30.50, 7.974455, −1.228222, 1.378938
31.00, 7.844169, −1.228117, 1.395777
31.50, 7.717995, −1.228010, 1.412615
32.00, 7.595742, −1.227902, 1.429452
32.50, 7.477227, −1.227793, 1.446286
33.00, 7.362281, −1.227683, 1.463119
33.50, 7.250745, −1.227571, 1.479951
34.00, 7.142467, −1.227458, 1.496781
34.50, 7.037306, −1.227344, 1.513609
35.00, 6.935128, −1.227229, 1.530435

What we claim is:

1. A method for determining the shape of a lens having equal conic surfaces to minimize spherical aberration, comprising:

(a) performing an optimization search to minimize an error function over a conic constant K to calculate the lens parameters apical radius R, conic constant K, and center thickness CT for a selected lens power, optical zone, edge thickness and material index of refraction;

(b) performing a calculation of paraxial focal point distance;

(c) performing an optical ray tracing calculation for a selected marginal ray height using the lens parameters apical radius R, conic constant K, center thickness CT and index of refraction to calculate a marginal ray intersection point;

(d) calculating the signed distance between the marginal ray intersection point and the paraxial focal point distance to determine the error function used in the optimization search; and (e) performing iterative calculations to determine the apical radius R and center thickness CT used in the error function of step (a) for a current value of K, lens power, optical zone, edge thickness, and material index of refraction until values of apical radius R and center thickness CT converge so as to provide the shape to be used for forming the lens.

2. The method of claim 1 wherein in step (a) where the optimization is via Newton-Raphson iteration.

3. The method of claim 1 wherein in step (c) the selected marginal ray height is 0.7071 times the optical zone divided by 2.

* * * * *